United States Patent
Saka et al.

(12)

(10) Patent No.: US 11,456,087 B2
(45) Date of Patent: Sep. 27, 2022

(54) LEAD WIRE FOR NARROW SPACE INSERTION

(71) Applicant: TOTOKU ELECTRIC CO., LTD., Tokyo (JP)

(72) Inventors: Kenji Saka, Ueda (JP); Hikaru Yamakoshi, Ueda (JP); Takashi Miyazawa, Ueda (JP)

(73) Assignee: TOTOKU ELECTRIC CO., LTD., Tokyo (JP)

( * ) Notice: Subject to any disclaimer, the term of this patent is extended or adjusted under 35 U.S.C. 154(b) by 0 days.

(21) Appl. No.: 16/832,527

(22) Filed: Mar. 27, 2020

(65) Prior Publication Data

US 2020/0312480 A1   Oct. 1, 2020

(30) Foreign Application Priority Data

Mar. 29, 2019   (JP) .............................. JP2019-068555

(51) Int. Cl.
*H01B 1/02*   (2006.01)
*A61B 8/12*   (2006.01)

(52) U.S. Cl.
CPC ............... *H01B 1/026* (2013.01); *A61B 8/12* (2013.01)

(58) Field of Classification Search
CPC ..................................................... H01B 1/026
See application file for complete search history.

(56) References Cited

U.S. PATENT DOCUMENTS

| | | | | |
|---|---|---|---|---|
| 2,392,388 A | * | 1/1946 | Joyce, Jr. | ............... H01B 3/445 310/265 |
| 3,314,786 A | * | 4/1967 | Kneip, Jr. | ............... H01L 39/00 420/426 |
| 6,328,822 B1 | * | 12/2001 | Ishida | ..................... A61L 29/02 148/436 |
| 2008/0119762 A1 | * | 5/2008 | Tateishi | ................ A61M 25/09 72/364 |
| 2018/0289925 A1 | * | 10/2018 | Palmer | ................ A61M 25/005 |
| 2018/0371580 A1 | * | 12/2018 | Sekiya | ....................... C22C 9/00 |

FOREIGN PATENT DOCUMENTS

| | | |
|---|---|---|
| JP | 2004-337249 A | 12/2004 |
| JP | 2018-143604 A | 9/2018 |

* cited by examiner

*Primary Examiner* — William D Young
(74) *Attorney, Agent, or Firm* — Sughrue Mion, PLLC

(57) ABSTRACT

To provide a lead wire for narrow space insertion that is easily inserted into an elongated small-diameter pipe or small-diameter tube such as an ultrasonic probe or an electrode catheter. The above-described problem is solved by a lead wire for narrow space insertion including a copper alloy wire having a conductor diameter within a range of 0.015 to 0.18 mm, and an insulating layer provided to an outer periphery of the copper alloy wire. A friction coefficient of an outermost surface layer of the insulating layer is within a range of 0.05 to 0.3, a tensile strength of the lead wire is within a range of 700 to 1,500 MPa, and a conductivity of the copper alloy wire is within a range of 60 to 90% IACS.

2 Claims, No Drawings

LEAD WIRE FOR NARROW SPACE INSERTION

FIELD OF THE INVENTION

The present invention relates to a lead wire for narrow space insertion, and more specifically to a lead wire that is easily inserted into an elongated small-diameter pipe or small-diameter tube such as an ultrasonic probe or an electrode catheter.

BACKGROUND ART

As described in Patent Documents 1 and 2, a conductive lead wire may be inserted into an elongated small-diameter pipe or small-diameter tube such as an ultrasonic probe or an electrode catheter to electrically connect a tip end portion thereof. In such a case, an operator inserts the lead wires one by one by hand, and thus it is desirable that the lead wire can be easily inserted with favorable workability.

PRIOR ART DOCUMENTS

Patent Documents

Patent Document 1: Japanese Laid-Open Patent Application No. 2004-337249
Patent Document 2: Japanese Laid-Open Patent Application No. 2018-143604

SUMMARY OF THE INVENTION

Problems to be Solved by the Invention

To ensure that the operator can easily insert the lead wire described above into an elongated small-diameter pipe or small-diameter tube without trouble, it is desirable that the lead wire have a certain strength without readily bending or breaking.

An object of the present invention is to provide a lead wire for narrow space insertion that is easily inserted into an elongated small-diameter pipe or small-diameter tube such as an ultrasonic probe or an electrode catheter.

Means for Solving the Problems

A lead wire for narrow space insertion according to the present invention is a lead wire including a copper alloy wire having a conductor diameter within a range of 0.015 to 0.18 mm, and an insulating layer provided to an outer periphery of the copper alloy wire. A friction coefficient of an outermost surface layer of the insulating layer is within a range of 0.05 to 0.3, a tensile strength of the lead wire is within a range of 700 to 1,500 MPa, and a conductivity of the copper alloy wire is within a range of 60 to 90% IACS. It should be noted that, hereinafter, the lead wire for narrow space insertion may be simply referred to as the "lead wire."

According to this invention, the lead wire has an outer diameter within the above-described range and a friction coefficient of the outermost surface of the insulating layer within the above-described range, and thus can be easily inserted into a narrow space of a small-diameter pipe, a small-diameter tube, or the like, and has favorable slidability in particular, even when inserted as a bundle, resulting in little interference between the wires, and the like. Further, because the lead wire has a rigid wire material having a tensile strength within the above-described range, when the operator inserts the lead wires one by one or collectively into a narrow space, breakage, buckling, and the like are unlikely to occur, the lead wires are easily inserted into the narrow space without trouble, and end faces of the lead wires are not worn or chipped during insertion. Furthermore, the lead wire also has favorable conductivity and can be preferably used as a low resistance lead wire.

In the lead wire for narrow space insertion according to the present invention, preferably the copper alloy wire contains 0.5 to 15 mass % of Ag, with a remaining portion being Cu and inevitable impurities.

In the lead wire for narrow space insertion according to the present invention, preferably the outermost surface of the insulating layer is a fluorine-based filler-containing layer, a liquid paraffin layer, or a nylon layer. According to this invention, the friction coefficient of the outermost surface is small, making the lead wire easy to insert and easy to adhere to another component by an adhesive.

Effect of the Invention

According to the present invention, it is possible to provide a lead wire for narrow space insertion that is easily inserted into an elongated small-diameter pipe or small-diameter tube such as an ultrasonic probe or an electrode catheter. As a result, the present invention is preferably applied to lead wires wired to narrow locations of small-diameter pipes, small-diameter tubes, and the like, such as ultrasonic probes, electrode catheters, robot arms, and the like, and further pipes and tubes connected thereto, inserted through narrow locations and small holes, wired as a bundle, and the like.

Embodiments of the Invention

A lead wire for narrow space insertion according to the present invention will be described. The present invention is not limited to the embodiments described below.

The lead wire for narrow space insertion according to the present invention is a lead wire including a copper alloy wire having a conductor diameter within a range of 0.015 to 0.18 mm, and an insulating layer provided to an outer periphery of the copper alloy wire. A friction coefficient of an outermost surface of the insulating layer is within a range of 0.05 to 0.3, a tensile strength of the lead wire is within a range of 700 to 1,500 MPa, and a conductivity of the copper alloy wire is within a range of 60 to 90% IACS.

This lead wire for narrow space insertion has an outer diameter within the above-described range and a friction coefficient of the outermost surface of the insulating layer within the above-described range, and thus can be easily inserted into a narrow space of a small-diameter pipe, a small-diameter tube, or the like, and has favorable slidability in particular, even when inserted as a bundle, resulting in little interference between the wires, and the like. Further, because the lead wire has a rigid wire material having a tensile strength within the above-described range, when the operator inserts the lead wires one by one or collectively into a narrow space, breakage, buckling, and the like are unlikely to occur, the lead wires are easily inserted into the narrow space without trouble, and end faces of the lead wires are not worn or chipped during insertion. Furthermore, the lead wire also has favorable conductivity and can be preferably used as a low resistance lead wire.

Each component will be described in detail.
(Copper alloy wire)
The copper alloy wire is configured by a copper alloy wire having a conductor diameter within a range of 0.015 to 0.18 mm. With the conductor diameter within this range, the lead wire for narrow space insertion can be inserted into a thin, narrow space. When the conductor diameter is less than 0.015 mm, the wire is too thin and thus may increase processing costs. On the other hand, when the conductor diameter exceeds 0.18 mm, it is difficult to say that the wire is a thin wire to be inserted into an elongated small-diameter pipe or small-diameter tube such as an ultrasonic probe or an electrode catheter, and it cannot be said that the wire sufficiently meets recent demands.

Desirably, the conductivity of the copper alloy wire is within a range of 60 to 90% of the International Annealed Copper Standard (IACS). By using a copper alloy wire having such characteristics, it is possible to exhibit the effects of the present invention. It should be noted that the tensile strength is a value of the lead wire for narrow space insertion that includes the insulating layer, and is within a range of 700 to 1,500 MPa. The wire material of the lead wire for narrow space insertion having a tensile strength within the above-described range is a rigid wire material and thus, when the operator inserts the lead wires one by one into a narrow space, breakage, buckling, and the like are unlikely to occur, the lead wires are easily inserted into the narrow space without trouble, and copper alloy end faces of the lead wires are not worn or chipped during insertion. It should be noted that elongation of the lead wire for narrow space insertion having such mechanical characteristics (tensile strength) is often within a range of 1 to 5%, for example.

The copper alloy wire, by having a conductivity within the range of 60 to 90% IACS, has desirable conduction performance as a lead wire which is easily inserted into an elongated small-diameter pipe or small-diameter tube. When the conductivity is less than 60% IACS, the wire has high resistance and thus may not be preferable as a lead wire for narrow space insertion. Further, while the conductivity may exceed 90% IACS, the lead wire for narrow space insertion having the tensile strength described above has a conductivity of roughly 90% IACS or less.

The type of copper alloy wire is not particularly limited as long as the wire has the above-described characteristics. While preferred examples of the copper alloy wire include a copper alloy wire containing 2 to 10 mass % of silver and a copper alloy wire containing 0.1 to 3.0 mass % of zirconium (Zr), the composition is not particularly limited as long as the wire is a copper alloy wire having the above-described mechanical characteristics and electrical characteristics. Further, a surface of the lead wire for narrow space insertion may be provided with a plating layer in accordance with each purpose such as improvement of conductivity, improvement of preliminary solderability, and suppression of solder thinning. As such a plating layer, a silver plating layer, a nickel plating layer, a tin plating layer, a gold plating layer, or the like having a thickness of about 0.1 to 2.0 μm can be selected as desired and used.

(Insulating Layer)

The lead wire for narrow space insertion is provided with an insulating layer that covers an entire length of the copper alloy wire or the entire length excluding end portions. The insulating layer is not particularly limited as long as the layer is provided around the copper alloy wire and has an insulation that prevents electrical contact between the lead wires, and may be directly provided on the outer periphery of the copper alloy wire, and may be provided with another layer interposed therebetween. Further, the insulating layer is preferably a resin that decomposes during soldering to facilitate soldering, and is preferably any one type or two or more types selected from polyurethane resin, nylon resin, polyester resin, epoxy resin, polyesterimide resin, polyamide resin, and polyamideimide resin, for example. Such an insulating layer can be provided by various methods, and is preferably provided by a method such as baking, for example. A thickness of the insulating layer is also not particularly limited, but preferably the layer is provided at a thickness within a range of 1.0 to 10 μm, for example. It should be noted that the insulating layer is preferably provided so that a withstand voltage (direct current) thereof is at least 200 V or greater.

The outermost surface of the insulating layer is provided with a layer (also referred to as "outermost surface layer") having a friction coefficient within a range of 0.05 to 0.3. It should be noted that, because this outermost surface layer is also included in the insulating layer, the entire insulating layer may be configured by an insulating layer having such a friction coefficient (the insulating layer and the outermost surface layer being the same), or only the outermost surface of the insulating layers may be configured by an outermost surface layer having such a friction coefficient. When the friction coefficient is less than 0.05 or exceeds 0.3, insertion into a narrow space of a small-diameter pipe, a small-diameter tube, or the like may no longer be easy. It should be noted that the friction coefficient is a result obtained by measurement by a slidability evaluating method (JIS C 3216-3: 2011, Annex B: Slidability test, B3 Dynamic friction testing method 1). Further, interference between the lead wires also readily occurs in a narrow space.

Preferred examples of the outermost surface layer include a fluorine-based filler-containing layer, a liquid paraffin layer, a nylon layer, and the like. The fluorine-based filler-containing layer is an insulating resin layer containing a fluorine-based filler having an average particle size of about 0.2 to 3.0 μm. The liquid paraffin layer is a layer configured by a material also called white oil and includes alkyl naphthene as the main component. The nylon layer is a layer composed of a nylon having a low friction coefficient, and preferred examples thereof include nylon 6, 66 nylon 66, and modified products thereof The insulating resin layer constituting the fluorine-based filler-containing layer is preferably the same or the same type of resin as the resin constituting the insulating layer described above. In this way, the insulating layer and the fluorine-based filler-containing layer have excellent compatibility, can exhibit excellent adhesion, and are unlikely to peel. The term "same type" means that the resins need not be completely the same, and may be resins capable of ensuring compatibility without impairing the excellent adhesion (including modified resins as well), or may be resins including a dispersant and other additives from the standpoint of dispersing the fluorine-based filler into the outermost surface layer. The fluorine-based filler may be fine particles configured to include any one or two or more selected from polytetrafluoroethylene (PTFE), tetrafluoroethylene—perfluoro alkyl vinyl ether copolymer (PFA), tetrafluoroethylene—hexafluoropropylene copolymer (FEP), tetrafluoroethylene—ethylene copolymer (ETFE), polyvinylidene fluoride (PVDF), polychlorotrifluoroethylene (PCTFE), and chlorotrifluoroethylene—ethylene copolymer (ECTFE). Examples of commercially available products include PTFE fine particles (manufactured by BYK, trade name: CERAFLOUR 998), PTFE fine particles (manufactured by DuPont-Mitsui Fluorochemical Co., Ltd., trade name: Teflon (registered trademark) PTFE TLP10E-1), PFA fine particles (DuPont-Mitsui Fluorochemical Co., Ltd., trade name: Teflon (registered trademark) PFE 9738-JN), FEP fine particles (DuPont-Mitsui Fluorochemical Co., Ltd., trade name: Teflon (registered trademark) FEP 120-JRB), and the like.

When the average particle size of the fluorine-based filler is less than the thickness of the outermost surface layer, the dispersion quantity can be easily adjusted, which is preferable. On the other hand, when the average particle size of the fluorine-based filler is greater than or equal to the thickness of the outermost surface layer, the fluorine-based filler is readily exposed on the surface of the outermost surface layer, and thus the fine particles of the fluorine-based filler that appear on the surface reduce a frictional force, which is preferable from the standpoint of slidability. It should be noted that the average particle size is measured by a laser diffraction-type particle size distribution measuring device. Further, the dispersion quantity of the fluorine-based filler, while differing according to the average particle size of the fluorine-based filler as well, is preferably, for example, within a range of 0.5 to 10 mass % relative to the total amount of resin constituting the outermost surface layer (the total of the resin constituting the outermost surface layer which is the same as or the same type as the insulating layer and the fluorine-based filler) when the average particle size is within a range of 0.2 to 3.0 µm, for example. With the dispersion quantity set within this range, the friction coefficient of the outermost surface layer can be set within a range of 0.05 to 0.3, and favorable slidability can be exhibited.

Each of these layers has a friction coefficient within the above-described range, and thus has favorable slidability and is preferably applied as the outermost surface layer of the lead wire wired to an elongated narrow location, such as an ultrasonic probe or an electrode catheter. Such an outermost surface layer is formed by being coated as an insulating layer or by being overcoated as an outermost surface layer on the insulating layer.

In particular, the lumen tube constituting the electrode catheter is configured by various fluororesins (PTFE, PFA, FEP, and PVDF), PEEK, polyimide, polypropylene, nylon elastomer (Pebax), urethane (TECOFLEX), polyethylene, polyester elastomer (Hytrel), styrene elastomer, silicone rubber, and the like. In this way, it is preferable to select and provide a material of the outermost surface layer that exhibits a preferred friction coefficient in relation to the material into which the lead wire for narrow space insertion is inserted.

(Fabrication of Lead Wire)

The lead wire for narrow space insertion is fabricated by preparing a copper alloy wire having a predetermined thickness (for example, a copper alloy wire having a diameter of 0.65 mm, or the like) and constituting a copper alloy wire, and drawing the copper alloy wire to a final wire diameter. At this time, silver plating or the like may be applied during the drawing process as necessary. Subsequently, tension annealing (heat treatment while applying tension) is performed as necessary at a temperature of, for example, about 300 to 400° C. and straightening is performed to fabricate a copper alloy wire composed of a copper alloy wire having a radius of curvature of 300 mm or greater, for example, a tensile strength within a range of 700 to 1,500 MPa, and a conductivity within a range of 60 to 90% IACS. Subsequently, for example, an insulating layer having a thickness of 2 to 10 µm and a friction coefficient within the above-described range is formed by a baking and coating method to fabricate a lead wire for narrow space insertion.

The means for fabricating the lead wire for narrow space insertion is not limited to the above-described method, and fabrication can be performed by various methods. For example, desirably, the temperature during baking and coating is a temperature at which the tensile strength, the conductivity, the radius of curvature, and the like of the copper alloy wire composed of the copper alloy wire do not reduce.

The radius of curvature of the lead wire for narrow space insertion including the copper alloy wire is at least 300 mm or greater, preferably has a straightness of 1,000 mm or greater, and more preferably has a straightness of 3,000 mm or greater. A radius of curvature within this range can be adjusted by tension annealing. A lead wire having favorable straightness is easy to wire into an elongated narrow location, and can be preferably applied as the lead wire for narrow space insertion according to the present invention. It should be noted that an upper limit of the radius of curvature is "completely straight." It should be noted that a more preferable lead wire for narrow space insertion according to the present invention is a lead wire to be inserted into a narrow space one by one or as a bundle, and includes a copper alloy wire having a conductor diameter within a range of 0.015 to 0.18 mm, an insulating layer provided to an outer periphery of the copper alloy wire (this insulating layer being a "baked insulating layer" baked and coated), and an outermost surface layer provided to an outermost surface of the insulating layer. A friction coefficient of the outermost surface layer is within a range of 0.05 to 0.3, a tensile strength of the lead wire is within a range of 700 to 1,500 MPa, a conductivity of the copper alloy wire is within a range of 60 to 90% IACS, and a radius of curvature of the lead wire has a straightness of 300 mm or greater. At this time, the outermost surface layer is preferably a fluorine-based filler-containing layer, a liquid paraffin layer, or a nylon layer, and more preferably a liquid paraffin layer or a nylon layer.

EXAMPLES

Hereinafter, the present invention is described more specifically through examples and comparative examples.

Example 1

A copper alloy wire (diameter: 0.65 mm) containing 4 mass % of silver was used, and was drawn to a diameter of 0.04 mm (processing ratio: 99.62%). The obtained copper alloy wire was tension-annealed at 350° C. (heat treatment time: 24 seconds), an outer periphery of the copper alloy wire was subsequently coated by baking polyurethane resin to form an insulating layer having a thickness of 0.005 mm, and nylon 66 having a thickness of 0.5 µm was further coated to form the outermost surface layer. Thus, the lead wire of Example 1 was obtained.

Examples 2 and 3

Examples 2 and 3 are cases in which the copper alloy wire was replaced with a copper alloy wire containing 2 mass % of silver and a copper alloy wire containing 10 mass % of silver, respectively, and otherwise all was made the same as Example 1 to obtain the lead wires of Examples 2 and 3.

Examples 4 and 5

Examples 4 and 5 are cases in which the outermost surface layer was replaced with a liquid paraffin layer having a thickness of 0.5 μm and a fluorine-based filler-containing layer having a thickness of 0.5 μm, respectively, and otherwise all was made the same as Example 1 to obtain the lead wires. It should be noted that the fluorine-based filler-containing layer is a fluororesin containing 3 mass % of PTFE fine particles (manufactured by BYK, trade name: CERAFLOUR 998, average particle size: 0.3 μm) with respect to the total amount of resin constituting the outermost surface layer. Thus, the lead wires of Examples 4 and 5 were fabricated.

Comparative Example 1

Comparative Example 1 is a case in which the outermost surface layer in Example 1 was not provided, and otherwise all was made the same as Example 1 to obtain the lead wire of Comparative Example 1.

Comparative Example 2

Comparative Example 2 is a case in which tension annealing was performed in Example 1, and otherwise all was made the same as Example 1 to obtain the lead wire of Comparative Example 2.

Comparative Example 3

An annealed copper wire was used instead of the copper alloy wire in Example 1, an outer periphery thereof was coated by baking polyurethane resin to form an insulating layer having a thickness of 0.005 mm, and an active nylon layer (nylon 66) having a thickness of 0.5 was further formed as the outermost surface layer. Thus, the lead wire of Example 3 was obtained.

[Measurement]

The obtained lead wires were measured for tensile strength, elongation, conductivity, radius of curvature, friction coefficient, and the like. Tensile strength and elongation values were obtained by measuring the obtained lead wires by a table-top-type precision universal testing machine (manufactured by Shimadzu Corporation, AGS-X). Conductivity values were obtained by measuring the obtained lead wires by a multimeter (manufactured by Hewlett-Packard Company, currently Keysight Technologies, 3468A). Radius of curvature values were obtained by measuring the radius of curvatures of the obtained lead wires by a scale after allowing the lead wires to stand in a natural state. It should be noted that the friction coefficients of the outermost surface layers were obtained by measuring the obtained lead wires by a slidability evaluating method (JIS C 3216-3: 2011, Annex B: Slidability test, B3 Dynamic friction testing method 1). Ease of insertion was evaluated by whether or not one obtained lead wire was easily inserted into a small-diameter pipe/tube composed of PFA material and having a diameter of 0.15 mm and a length of 20 mm. The obtained lead wire was evaluated as "o" if the wire could be inserted without buckling at the entrance of the small-diameter pipe/tube and easily passed through the small-diameter pipe/tube even after insertion, "Δ" if the wire could be inserted without buckling at the entrance of the small-diameter pipe/tube, but could not be easily passed through the small-diameter pipe/tube after insertion and thus easily buckled, and "x" if the wire easily buckled at the entrance of the small-diameter pipe/tube and easily buckled in the small-diameter pipe/tube even after insertion.

TABLE 1

| | Tensile strength MPa | Conductivity % IACS | Straightness R (mm) | Friction coefficient | Insertability |
|---|---|---|---|---|---|
| Example 1 | 1050 | 80 | 3000 | 0.07 | o |
| Example 2 | 850 | 90 | 3000 | 0.07 | o |
| Example 3 | 1350 | 70 | 3000 | 0.07 | o |
| Example 4 | 1050 | 80 | 3000 | 0.17 | o |
| Example 5 | 1050 | 80 | 3000 | 0.07 | o |
| Comparative Example 1 | 1050 | 80 | 3000 | 0.55 | Δ |
| Comparative Example 2 | 650 | 85 | 3000 | 0.07 | x |
| Comparative Example 3 | 250 | 100 | 1000 | 0.07 | Δ |

[Evaluation]

From the results in Table 1, in the lead wires having favorable insertability of the Examples 1 to 5, the friction coefficient of the outermost surface of the insulating layer was in the range of 0.07 to 0.17, and the tensile strength of the lead wire was in the range of 850 to 1,350 MPa. Further, the lead wires of Examples 1 to 5 had high conductivity in the range of 70 to 90% IACS. In Comparative Examples 1 to 3, the insertability deteriorated because the friction coefficient was large or the tensile strength was small. From the examples described above, the preferred lead wire had a tensile strength within a range of 700 to 1,500 MPa, a friction coefficient within a range of 0.05 to 0.3, and a conductivity within a range of 60 to 90% IACS.

What is claimed is:

1. A lead wire for insertion by an operator one by one or collectively into a narrow space, comprising:
    a copper alloy wire having a conductor diameter within a range of 0.015 to 0.18 mm; and
    an insulating layer provided to an outer periphery of the copper alloy wire by baking, a thickness of the insulating layer is 1.0 to 10 μm,
    a friction coefficient of only an outermost surface layer of the insulating layer being within a range of 0.05 to 0.3,
    a tensile strength of the lead wire being within a range of 700 to 1,500 MPa,
    a conductivity of the copper alloy wire being within a range of 60 to 90% International Annealed Copper Standard (IACS);
    the outermost surface layer of the insulating layer being a liquid paraffin layer or a nylon layer;
    a radius of curvature of the lead wire for narrow space insertion is at least 300 mm or greater; and
    the copper alloy wire contains 0.5 to 15 mass % of Ag, with a remaining portion being Cu and inevitable impurities.

2. A lead wire for insertion by an operator one by one or collectively into a narrow space, comprising:
    a copper alloy wire having a conductor diameter within a range of 0.015 to 0.18 mm; and
    an insulating layer provided to an outer periphery of the copper alloy wire by baking,
    a friction coefficient of only an outermost surface layer of the insulating layer being within a range of 0.05 to 0.3,
    a tensile strength of the lead wire being within a range of 700 to 1,500 MPa,
    a conductivity of the copper alloy wire being within a range of 60 to 90% International Annealed Copper Standard (IACS);
    the outermost surface layer of the insulating layer being a liquid paraffin layer or a nylon layer;

a radius of curvature of the lead wire for narrow space insertion is at least 300 mm or greater; and the copper alloy wire contains 0.5 to 15 mass % of Ag, with a remaining portion being Cu and inevitable impurities.

* * * * *